United States Patent [19]
Meyer

[11] Patent Number: 5,756,075
[45] Date of Patent: May 26, 1998

[54] APPARATUS AND METHOD FOR SUNLESS TANNING

[75] Inventor: Thomas A. Meyer, Germantown, Tenn.

[73] Assignee: Schering-Plough HealthCare Products, Inc., Memphis, Tenn.

[21] Appl. No.: 712,944

[22] PCT Filed: Mar. 25, 1993

[86] PCT No.: PCT/US93/02586

§ 371 Date: Feb. 15, 1995

§ 102(e) Date: Feb. 15, 1995

[87] PCT Pub. No.: WO94/04130

PCT Pub. Date: Mar. 3, 1994

Related U.S. Application Data

[63] Continuation of Ser. No. 387,757, Feb. 15, 1995, abandoned.

[51] Int. Cl.$^6$ .............................. A61K 7/42; A61K 7/44; A61K 7/00

[52] U.S. Cl. .............................. 424/59; 424/60; 424/400; 424/401

[58] Field of Search .............................. 424/59, 60, 63, 424/400, 401

[56] References Cited

U.S. PATENT DOCUMENTS

| | | | |
|---|---|---|---|
| 2,176,923 | 10/1939 | Nitardy | 221/60 |
| 2,853,423 | 9/1958 | La Via | 424/60 |
| 2,949,403 | 8/1960 | Andreadis et al. | 424/59 |
| 3,177,120 | 4/1965 | Black et al. | 167/90 |
| 3,290,017 | 12/1966 | Davies et al. | 259/114 |
| 3,403,207 | 9/1968 | Kreps et al. | 424/60 |
| 3,608,709 | 9/1971 | Pike | 206/47 A |
| 3,651,931 | 3/1972 | Hsiung | 206/47 A |
| 3,756,389 | 9/1973 | Firth | 206/47 A |
| 3,809,224 | 5/1974 | Greenwood | 206/219 |
| 3,983,994 | 10/1976 | Wyslotsky | 206/219 |
| 4,193,989 | 3/1980 | Teng et al. | 424/60 |
| 4,434,154 | 2/1984 | McShane | 424/60 |
| 4,458,811 | 7/1984 | Wilkinson | 206/219 |
| 4,466,805 | 8/1984 | Welters et al. | 8/406 |
| 4,496,046 | 1/1985 | Stone et al. | 206/219 |
| 4,608,043 | 8/1986 | Larkin | 604/87 |
| 4,609,544 | 9/1986 | Herlihy | 424/59 |
| 4,772,471 | 9/1988 | Vanlerberghe et al. | 424/450 |
| 4,968,497 | 11/1990 | Wolfram et al. | 424/59 |

FOREIGN PATENT DOCUMENTS

| | | | |
|---|---|---|---|
| 424282 | 4/1991 | European Pat. Off. | 424/59 |
| 425324 | 5/1991 | European Pat. Off. | 424/59 |
| 1252400 | 12/1960 | France | 424/59 |
| 2062016 | 5/1981 | United Kingdom | 424/59 |
| 2180215 | 3/1987 | United Kingdom | 424/59 |

OTHER PUBLICATIONS

*Chemical Abstracts*, vol. 72, abstract 103635b.
*Chemical Abstracts*, vol. 95, abstract 30226g.
E. Wittgenstein and H. Berry, "Reaction of Dihydroxyacetone (DHA) with Human Skin Callus and Amino Compounds", *Journal of Investigative Dermatology*, vol. 36, pp. 283–285 (1961).
A. Meybeck, "A Spectroscopic Study of the Reaction Products of Dihydroxyacetone with Aminoacids," *Journal of the Society of Cosmetic Chemists*, vol. 28, pp. 25–35 (1977).
M.F. Bobin, M.C. Martini and J. Cotte, "Effects of Color Adjuvants on the Tanning Effect of Dihydroxyacetone," *Journal of the Society of Cosmetic Chemists*, vol. 35, pp. 265–272 (1984).
D. Debrovner, "Bottled Sunshine," *American Druggist*, Jul. 1992, pp. 42, 47 and 49.
"Sonnenschutzmittel und Bräunungs–Gel," in *Riechstoffe, Aromen, Körperpflegemittel*, vol. 28, No. 5, May 1970, p. 186.

*Primary Examiner*—Shelley A. Dodson
*Attorney, Agent, or Firm*—Robert A. Franks; John J. Maitner

[57] ABSTRACT

Apparatus for simulating skin tanning comprises a receptacle containing a fluid comprising dihydroxyacetone, a receptacle containing a fluid comprising a primary amine, and dispensing means for simultaneously or sequentially providing desired amount of dihydroxyacetone and amine.

22 Claims, 5 Drawing Sheets

APPARATUS AND METHOD FOR SUNLESS TANNING

CROSS-REFERENCE TO RELATED APPLICATIONS

The present application is a continuation of Ser. No. 08/387,757 filed on Feb. 15, 1995 and now abandoned, which itself is the United States national application corresponding to International Application No. PCT/US93/02586, filed Mar. 25, 1993, published as WO94/04130 Mar. 3, 1994 and designating the United States, which PCT application is in turn a continuation of U.S. patent application Ser. No. 07/934,601 filed Aug. 24, 1992 and now abandoned, the benefit of which applications are claimed pursuant to the provisions of 35 U.S.C. §§ 120, 363 and 365(C).

FIELD OF THE INVENTION

This invention relates to apparatus which is useful in the simulated tanning of skin. More particularly, the invention relates to apparatus which is used in the treatment of skin with dihydroxyacetone compositions, to form a brownish coloration thereon.

INTRODUCTION TO THE INVENTION

It has long been known that certain compounds form pigments when applied to the skin. Products containing dihydroxyacetone (frequently simply abbreviated to "DHA") have been marketed since the early 1960's, and have been found satisfactory by many persons who wish to give their skin the appearance of an attractive tan, but do not desire to risk the now well-appreciated health hazards of exposure to solar or artificially-generated ultraviolet radiation.

However, some persons have not obtained the desired results from DHA applications. A small number of individuals develop a coloration which tends to appear yellowish or orange. Some others, probably due to perspiration, rubbing or washing during the slow generation of color as skin components react with DHA, or to a lack of care to evenly apply the DHA, develop uneven coloration.

The chemistry of DHA-skin interaction has been investigated by several workers. Wittgenstein and Berry published a paper "Reaction of Dihydroxyacetone (DHA) with Human Skin Callus and Amino Compounds," in *The Journal of Investigative Dermatology*, Vol. 36, pages 283–286 (1961), describing work to characterize the browning phenomenon. They reported that DHA reacts with a number of compounds, including ammonia and amino acids, to form a brown color, and theorized that skin browning is due to the reaction of DHA with free amino groups in the skin, the amino groups probably being on arginine molecules which are present in skin proteins.

A. Meybeck published "A Spectroscopic Study of the Reaction Products of Dihydroxyacetone with Aminoacids" in *Journal of the Society of Cosmetic Chemists*, Vol. 28, pages 25–35 (1977), and characterized brown pigments formed from the reaction of DHA with amino and other acids at 100° C. Further experiments at 37° C. were conducted to better simulate reactions which may occur in the skin: DHA was reacted with the amino acids glycine, lysine, alanine, serine and arginine, but only glycine and lysine produced significant amounts of pigment after 24 hours. It was concluded that DHA must act by initially condensing with free amino acids at the skin surface, followed by polymerization and linking to proteins in the stratum corneum, probably through lysine side chains.

A further study was reported by M. F. Bobin, M. C. Martini and J. Cotte, "Effects of Color Adjuvants on the Tanning Effect of Dihydroxyacetone," *Journal of the Society of Cosmetic Chemists*, Vol. 35, pages 265–272 (1984). This work involved measuring the rate of color development after mixing DHA and various amino acids or their derivatives, and applications of DHA and methionine sulfoxide in vivo. It was concluded that methionine sulfoxide is a useful adjuvant to DHA, as the combination provided rapid color development, plus a more intense and long lasting color than would be obtained with only DHA. This result was thought to result from the affinity of methionine sulfoxide for keratin.

*Chemical Abstracts*, Vol. 95, abstract 30226g (1981) summarizes a German patent document (3,037,497) pertaining to dyeing skin, hair, feathers, fur, etc. by treating with a mixture of DHA and an amino acid sulfoxide. When DHA and methionine sulfoxide were applied in cream formulations, skin turned a deep brown color after three hours and the color was more resistant to washing than that obtained with only DHA.

Black et al., in U.S. Pat. No. 3,177,120, discussed the problem of including DHA and amino group-containing sunscreens together in a formulation, and concluded that only sunscreens free from amino groups should be used, to prevent formation of a yellow or brown color in the storage container; color formation is also said to be accompanied by inactivation of both the DHA and sunscreen.

In spite of the teachings in the art relating to the use of DHA with α-amino acids and their derivatives, it has been found that color formed thereby does not have a desired substantivity, or resistance to removal by rubbing or washing. Thus, it is desired to provide apparatus and a method for browning skin to form simulated tans having improved substantivity and colors which closely resemble those obtained from exposure to ultraviolet radiation.

SUMMARY OF THE INVENTION

The invention, in one aspect, provides an apparatus for imparting artificial tan to skin, comprising: a receptacle containing a fluid formulation comprising dihydroxyacetone; a receptacle containing a fluid formulation comprising a primary amine; and dispensing means for simultaneously or sequentially providing desired amounts of dihydroxyacetone and amine. The invention also includes a method for imparting artificial tan to skin, comprising simultaneously or sequentially contacting the skin with dihydroxyacetone and a primary amine. Also included is a composition for immediate application to skin, comprising dihydroxyacetone, at least one primary amine and a suitable carrier.

DETAILED DESCRIPTION OF THE INVENTION

The invention will be described with reference to the accompanying drawings. In the description and claims, all percentages are expressed on a weight basis, unless otherwise noted.

In accordance with the invention, there is provided apparatus for imparting a simulated tan to skin, the apparatus having separate compartments for a formulation containing dihydroxyacetone and a formulation containing a primary amine. As previously noted, it is important to prevent the mixing of the components until a user is ready to make a skin application, to prevent premature reaction and color formation. The apparatus can be configured to simultaneously dispense the formulations, in desired amounts, or to sequentially dispense them. If sequentially dispensed, the formulations can be mixed before spreading onto the skin, or can be spread in the order of dispensing.

Figure 1:
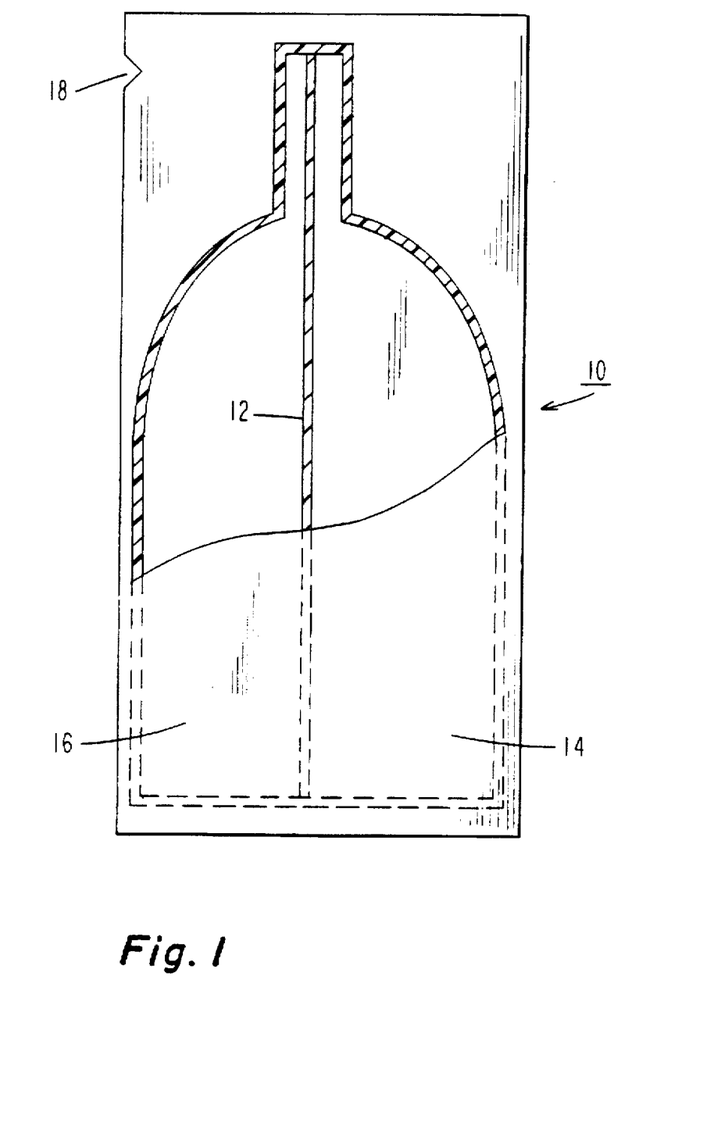
FIG. 1 is a cross-sectional view of a pouch container having two compartments.

Referring to FIG. 1, there are shown the features of a two-compartment pouch 10. Included is septum 12 which, in the least complex embodiment where the pouch comprises heat sealed layers of a thermoplastic substance, is merely a heat sealed seam to divide the volume of the pouch. This septum divides the volume into chambers 14 and 16. Tearing notch 18 can be provided to facilitate removal of the top of the pouch, when it is desired to dispense formulations contained therein. This embodiment will be used primarily for single-use quantities, the pouch holding an appropriate quantity for application once to the whole body or a portion thereof, such as only the face.

As an alternative to a tearing notch, the user can simply cut off the top of the pouch with scissors or a knife. Further, rather than dispensing the two formulations from the pouch in two streams, as would be done with the configuration depicted, septum 12 can be made frangible; applying pressure with the fingers to one side of the pouch will rupture the septum and permit mixing of the formulations by sequentially applying pressure to the two sides, after which a single composition containing both DHA and amine can be applied. Of course, such mixing should only be conducted immediately before use.

For sequential application of the two formulations, another tearing notch (not shown) can be provided on the opposite side of the pouch from notch 18, and the septum can be extended to the uppermost limit of the pouch. This will permit only one compartment to be opened by pulling above a notch.

Figure 2:
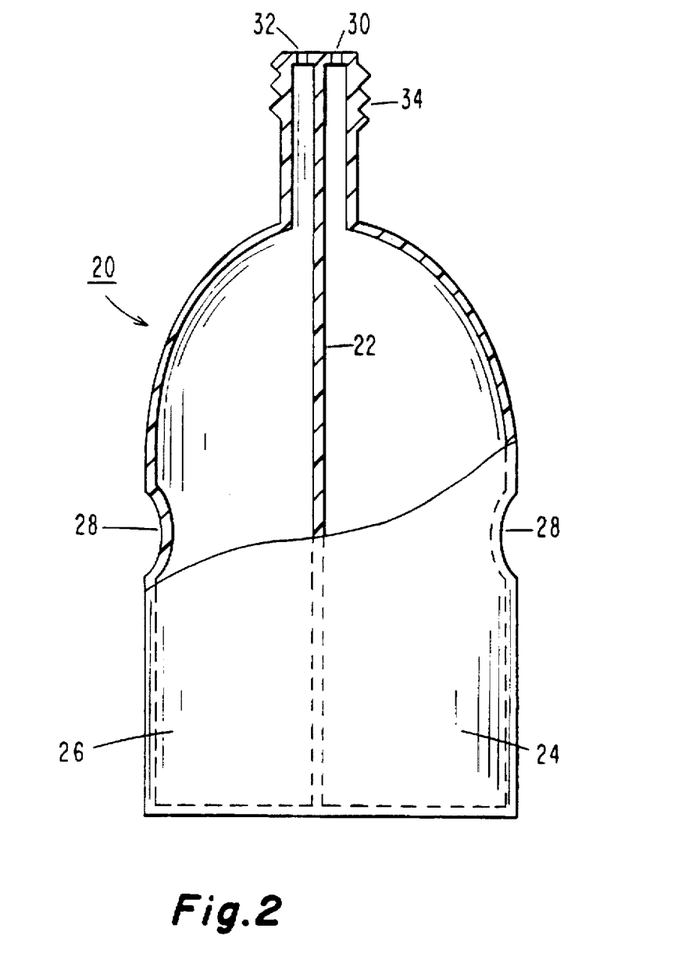
FIG. 2 is a cross-sectional view of a squeeze bottle having two compartments.

FIG. 2 is a view of a squeeze bottle 20, which is provided with septum 22 to form two compartments 24 and 26. The bottle is conveniently formed by molding with thermoplastic substances, as is well known in the art. In a typical embodiment, threads 34 will be provided for closure with a conventional screw cap (not shown). The threads will not be needed if the bottle is closed by alternative means, such as a pressed on flip cap.

Preferably, gripping indentations 28 are provided, to ensure that the bottle is squeezed in locations which will apply approximately uniform pressure to the two compartments, i.e., not to a less deformable area such as that directly over the septum. Upon pressure application, formulations are dispensed from the compartments through orifices 30 and 32.

The bottle can be used for sequential applications of DHA and amine, by providing separate closures for the two orifices. As an example, individual snap caps can be provided over the orifices. The user would be required to dispense an appropriate amount of a component, rub that component into the skin and, immediately or after a prescribed time, apply the second component to the skin in a similar manner. Application of equal amounts of the components can be accomplished with sufficient accuracy by noting the lengths of dispensed fluids on the skin; the bottle can be provided with length scales marked thereon to make this more convenient.

Figure 3:
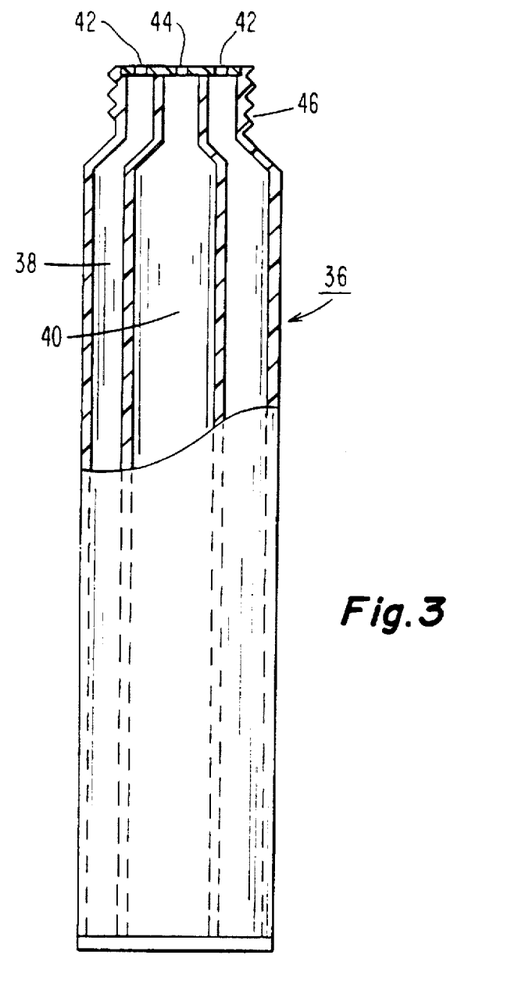
FIG. 3 is a cross-sectional view of a dual-compartment tube container.

Referring now to FIG. 3, there is shown a cross-sectional view of a collapsible tube assembly 36 which is useful in the invention. As shown, the outer tube 38 surrounds the inner tube 40, and contents of the outer and inner tubes can be discharged through outlets 42 and 44, respectively, by squeezing the assembly. A threaded area 46 is provided for attachment of a closure (not shown). Any desired number of outlets can be provided for the tubes and any desired type of closure can be used, the invention not being restricted to a threaded cap.

The assembly can be fabricated from any materials normally utilized for tubes dispensing medications, cosmetic materials, hygiene products such as toothpastes, cleaning compositions and the like, subject to the usual requirement that the materials of construction do not react with formulations contained therein to an appreciable extent during at least the expected storage term. Frequently used materials include metals, polymers and composites, including laminates. Typically, the assembly will be closed at its bottom end by crimping or heat sealing, depending upon the materials of construction. To assure that formulations are dispensed in predetermined relative amounts from the outer and inner tubes, means (not shown) such as a key can be provided at the bottom of the assembly for uniformly collapsing the tubes; as the bottom of the assembly is wound around a rotated key, approximately the same pressure will be applied to the two tubes.

Figure 4:
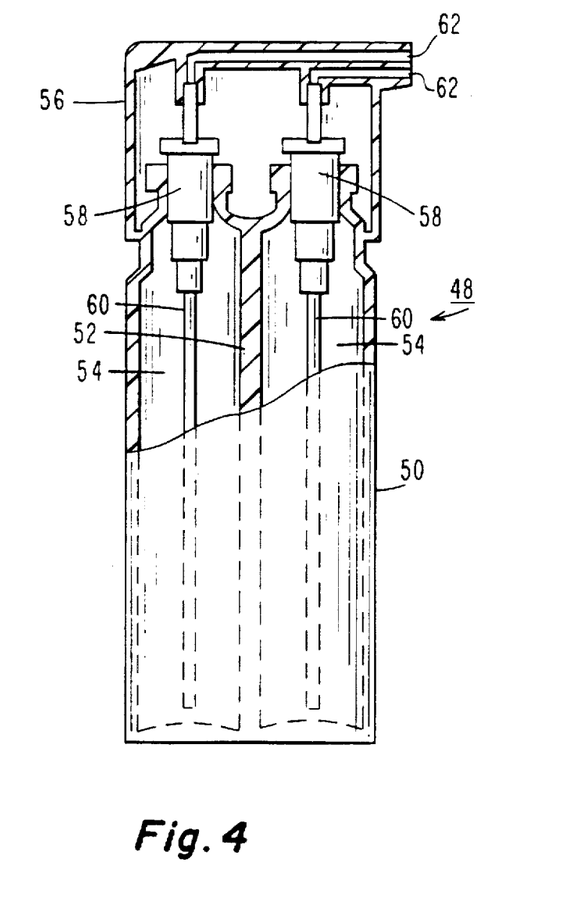
FIG. 4 is a cross-sectional view of a container having two compartments and a dual pump dispenser.

A further apparatus is shown in cross-section as FIG. 4. In this figure, dispensing container 48 comprises bottle 50, having dividing septum 52 which forms two compartments 54 having any desired geometry. Cap 56 is adapted to fit over the outlets of pumps 58, mounted to close the compartments and which can be any of the well-known spring loaded check valve pumps such as are used with hand lotions and other cosmetic products. Pressing down on the cap causes formulations to be simultaneously dispensed from conduits 62; releasing the cap permits it to rise under pressure from springs in the pumps, simultaneously reloading the pumps with stored formulations through dip tubes 60.

This apparatus requires no particular care on the part of the user to obtain a correct ratio of the formulations, in cases where the formulations are to be simultaneously dispensed and applied, but permits complete separation of the components until dispensing. By providing separate caps over the pumps, it would be possible to dispense the formulations at different times, should this be desired. In either embodiment, reproducible amounts will be dispensed simply by pressing the cap down for its full length of travel each time, without any need for a user to make measurements.

Figure 5:
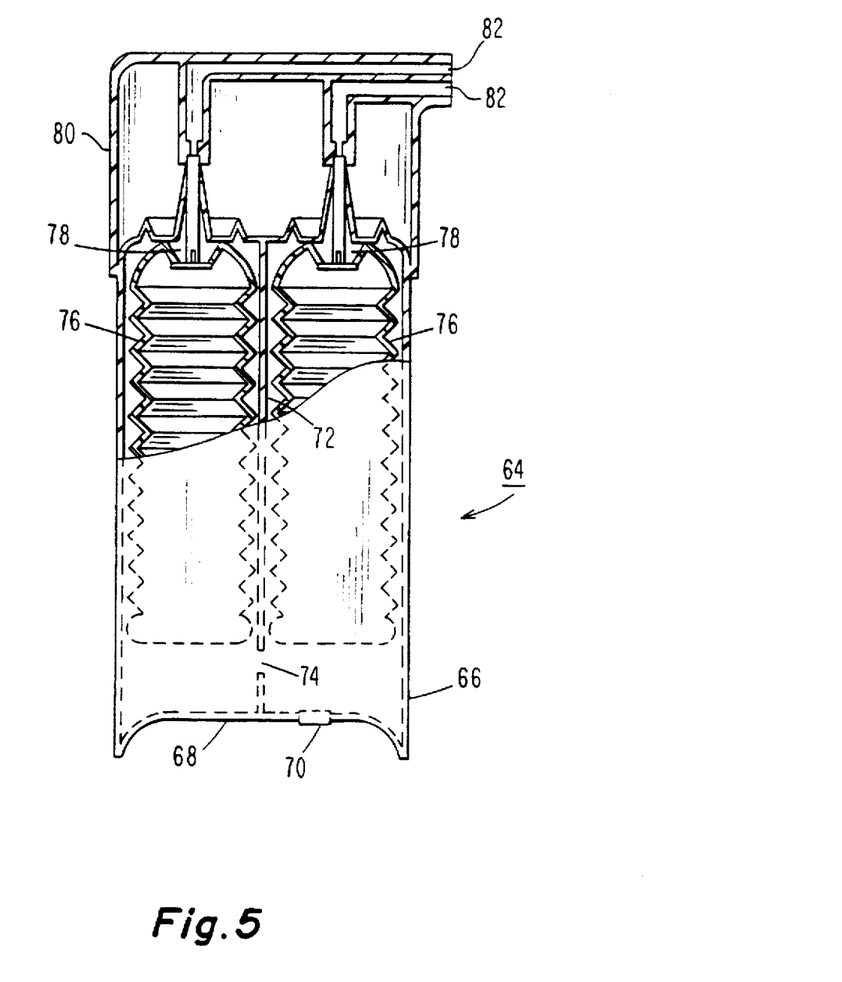
FIG. 5 is a cross-sectional view of a dual-compartment pressurized dispensing container.

FIG. 5 relates to a pressurized aerosol container which can be used to dispense two components simultaneously. Container 64 comprises external shell 66, with bottom closure 68 attached; preferably, both of these components will be fabricated from metals, with the bottom closure crimped or welded to the shell. Gas filling port 70 is provided to seal the container after a pressurizing gas is introduced.

The container is divided by barrier 72, which is provided with one or more perforations 74 near the bottom of the container, to equalize gas pressure in the two sections formed by the barrier. Each section has an accordion-pleated bag 76, preferably fabricated from a plastic material, to contain a formulation, the bags each being connected to an aerosol valve 78 which is actuated to release formulation by its depression into the container. Cap 80 is utilized to simultaneously depress the valves, and directs formulations through conduits 82 for application to a desired area.

This apparatus has the advantages of dispensing desired relative amounts of the contained formulations without any special care on the part of the user, and being very simple to use. By using plastic bags to contain the formulations, the aerosol container needs not be chemically compatible with the formulations, and the propellant will not normally be in contact with the formulations. Of course, costs can be reduced by changing the design to make use of sealed compartments having pistons driven by gas pressure to force formulations out through the valves, but piston sealing, compatibility of construction materials with the formulations and other considerations will complicate the product design. Many alternatives will be apparent to those skilled in aerosol container packaging.

Another useful package for the present invention has two compartments, divided by a removable or frangible barrier. An example is the collapsible tube of U.S. Pat. No. 2,176,923 to Nitardy, where two substances are separated in a tube by a transverse partition which is a collapsible disk having a central aperture; expressible plugs in the aperture are removed by applying pressure to the bottom of the tube, causing the substances to mix. U.S. Pat. No. 3,290,017 to Davies et al. is related, having a disc which can be moved from a barrier position to a mixing position in a tube by external finger pressure.

A further example is found in U.S. Pat. No. 3,608,709 to Pike, where a multiple-compartment laminated pouch is described. This pouch, when external pressure is applied, will form a single compartment by breakage of the internal barrier, permitting two formulations contained therein to mix. Other packages having frangible internal barriers are shown in the following U.S. Pat. Nos. 3,756,389; 4,458,811; and 4,608,043; these can be adapted for use in the present invention.

U.S. Pat. No. 3,809,224 to Greenwood shows another useful package, having an external clamp divider seal which can be removed to permit mixing of components stored separately when the clamp is in place.

Each of these packages having a frangible or removable barrier will be suitable for single use unit packaging only, since it will be necessary to use the entire contents of the package promptly after the DHA and amine formulations are mixed, due to the previously discussed reaction.

The foregoing is a description of representative packaging techniques for maintaining and dispensing a formulation comprising dihydroxyacetone and a formulation comprising a primary amine. Both formulations must be fluid, that is, capable of flow under the influence of gravity or a moderate externally applied pressure. Examples of useful fluid formulations are ointments, dispersions such as creams and lotions, gels, solutions, and the like, each of which (and preparative techniques therefor) are very well known to those skilled in the formulating art.

Typically, both formulations which are to be used together will be of the same type, e.g., if one is a gel, the other also will be a gel to facilitate application and mixing. However, it is not always necessary to observe this general principle.

Amines which are useful in preparing the formulations of the invention have the general formula $RNH_2$, where R is selected from the group consisting of:

—$(CH_2)_n COOH$;
—$(CH_2)_x COOR'$;
—$(CH_2)_y CH_3$;
—$(CH_2)_x OH$;
—$CH_2 (C_6H_5)$;
—$C(O)(C_6H_5)$;
—$(CH_2)_x CH(OR')_2$;
—$(CH_2)_x OR'$;
—$(OCH_2CH_2)_z NH_2$;
cyclic groups containing N, O or S in the ring;
—$Si(OH)_3$; and
—$Si(OR')_3$;

wherein n is an integer of at least 2, x is an integer of up to 22, y is an integer of 5 to about 22, z is an integer of up to about 10, and R' is an alkyl group having up to about 10 carbon atoms. The term "alkyl," is used herein to refer to substituted or unsubstituted groups, branched or unbranched, permissible substituents being halogens, nitrogen-containing groups, sulfur-containing groups, hydroxy groups, carbonyl-containing groups, and the like. In general, the amount of heteroatom substitution in an alkyl group will be less than one such atom per each five carbon atoms in the group and, usually, the alkyl groups will be hydrocarbon groups. Where "$CH_2$" appears in the groups listed as possibilities for R, above, these $CH_2$ units may be substituted similarly to the alkyl groups. It should be noted that more than one amino group can be present in a compound; amino groups are not considered to be "heteroatom-containing" for purposes of this invention.

Cyclic groups having N, O or S in the ring include those based upon aziridine, azetidine, pyrrolidine, pyrrole, piperidine, diazole, imidazole, tetrazole, oxole, oxolane, thiole, thiazole and the like. In particular, amines having an oxole or oxolane group have been found useful in the invention.

Volumes and active ingredient concentrations of dispensed formulations should be chosen to provide molar ratios of DHA to amine about 0.5 to about 10. More preferably, the ratios should be about 1 to about 5. Still more preferred are molar ratios about 1 to about 3. If the number of moles of DHA exceed the number of moles of amine, a portion of the DHA will remain free to react with amino groups in the skin, increasing the substantivity of the color formed; thus, a molar excess of DHA is preferred. Although the rate of color formation in the skin (with free amino groups present there) is considerably slower than that of DHA with provided primary amine on or near the skin surface, color formed in the skin is more resistant to removal by washing and abrasion. For this reason, it is preferable to establish both the early and frequently more intense color on the skin surface, and the more permanent but slower forming color in the skin layers.

It has been found that pH at the time of application affects the resulting color. In general, either the DHA formulation or the amine formulation should be able to establish pH values about 3 to about 13 locally when applied to the skin. More preferred are values about 7 to about 11, with values about 9 to about 10 being particularly preferred with some formulations. The optimal pH for a given amine application will be somewhat dependent upon the $pK_a$ of that amine, and can be determined by applying formulations having different pH values to the skin. For n-Dodecylamine, having a $pK_a$ of 10.63, a more reddish hue forms when the pH is much lower than 9 or 10, while a more yellowish hue forms at much higher pH values.

To compare simulated tans created by different means, it is helpful to have an objective, instrumental measurement of colors and intensities. Accordingly, a method has been developed using a Minolta Chroma Meter CR-200, which uses reflected light from a surface and gives results in terms of the CIE (International Commission on Illumination) tristimulus values. These values are subsequently transformed mathematically into the L* a* b* color space, wherein the magnitudes of changes in hue and intensity of color correspond closely with those percieved by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y axis, to give quantitative color information: "metric chroma" is the length of a line from the origin (a*=0, b*=0) to the point of a sample reading, while "metric hue angle" is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter is used to measure natural tans with a number of subjects, to establish a target for the appearance of tans produced by DHA reactions. In general, it is found that points on a chromaticity plot for dark tans will have b* from about 19 to about 24, with a* ranging from about 10 to about 14. For medium tans, b* will be about 20 to about 24, with a* from about 9 to about 12. For light tans, b* will be about 18 to about 20, with a* about 7 to about 10. Rather than being a point, the target color is represented by the area on the plot where natural tans lie. Values of metric chroma increase steadily as tans progress from light to medium, but increase much more slowly as tans become more dark than "medium." In contrast, values of metric hue angle overlap significantly for light, medium and dark tans, except for very dark tans which have increased redness (decreased metric hue angle).

Metric lightness is the third required parameter for characterizing natural tans. L* values decrease as tans become darker, a difference of about one unit being discernable to a trained observer. For natural tans, L* ranges from about 47 to about 53 for dark tans, about 54 to about 57 for medium tans and about 58 to about 64 for light tans.

The meter is also used to measure the characteristics of simulated tans obtained using only DHA applications. Several subjects are treated with an oil in water emulsion containing 5 percent DHA, with applications (2 mg DHA/cm$^2$) being made once each day for four days. After the first day, values for b* are about 13 to about 21, the a* values are about 3 to about 8 and L* values are about 63 to about 74. After two days, b* is about 15 to about 23, a* is about 5 to about 8 and L* is about 62 to about 72. After the third day, b* is about 16 to about 23, a* is about 5 to about 9 and L* is about 61 to about 71. After four days, b* is about 17 to about 24, a* is about 5 to about 9 and L* is about 61 to about 70. The hues for all but a few of the readings are more yellowish than the tan target area, and all but a few of the readings indicate tans more light than natural tans, even though comparable levels of metric chroma are generated. It can generally be stated that simulated tans using only DHA are more yellow and lighter than natural tans having similar extents of color formation.

The following examples are provided to illustrate various aspects of the invention, and are not to be construed as limiting the invention in any manner.

EXAMPLE 1

A gel containing 5 percent n-Dodecylamine is prepared, using the following components:

| | |
|---|---|
| 70.5 grams | Alcohol SD40-2 |
| 5 grams | Dodecylamine |
| 20 grams | Water |
| 1.5 grams | Hydroxypropylcellulose |
| 3 grams | Hydrochloric acid, 6N |

The gel is prepared by dissolving the amine in the alcohol, slowly adding the water, with stirring, to obtain a clear solution, adding the hydroxypropylcellulose with mixing, continuing mixing until the mixture is free of lumps, and adding the hydrochloric acid to obtain pH values of 9 to 9.5.

The hydroxypropylcellulose is sold as Klucel HF™ by Hercules Inc., Wilmington, Del. U.S.A.

EXAMPLE 2

A gel containing 10 percent n-Dodecylamine is prepared, using the procedure and components of the preceding example, and the following amounts:

| | |
|---|---|
| 70.0 grams | Alcohol SD40-2 |
| 10.0 grams | Dodecylamine |
| 11.5 grams | Water |
| 1.5 grams | Hydroxypropylcellulose |
| 7.0 grams | Hydrochloric acid, 6N |

EXAMPLE 3

A gel containing 10 percent n-Dodecylamine is prepared with remaining ingredients as in the preceding example, but using 14 grams of water and 4.5 grams of hydrochloric acid. This gel has a pH about 10.

EXAMPLE 4

A gel is prepared from the following components:

| Part | Grams | Component |
|---|---|---|
| A | 65.45 | Water |
| | 1.44 | Polyquarternium-10 |
| B | 19.16 | Alcohol SD40-2 |
| C | 0.17 | Water |
| | 0.02 | Citric acid |
| D | 4.78 | Water |
| | 7.10 | Dihydroxyacetone |
| | 0.10 | d,1-Panthenol |
| | 0.05 | Aloe concentrate |
| E | 1.44 | Polysorbate-80 |
| | 0.29 | Fragrance |

The gel, containing 7.10 percent DHA, is prepared by adding the Polyquarternium-10 to the water of part A, with stirring until the mixture is thick (about one hour). The alcohol of part B is added slowly, with stirring, to the part A mixture to form a uniform gel. Citric acid is dissolved in the water of part C, then mixed into the gel. The part D ingredients are dissolved in the water of that part, then mixed into the gel. Finally, the fragrance and Polysorbate-80 are mixed, and combined with the gel.

To 50 grams of the foregoing gel are added 21 grams of 50 percent (in water) Alcohol SD40-2, to prepare a gel containing 5 percent DHA.

The polyquaternium-10 is available from Amerchol Corporation, Edison, N.J. U.S.A. as Ucare Polymer JR-30M™. The polysorbate-80 is sold by ICI Americas Inc., Wilmington, Del. U.S.A. as Tween 80™.

EXAMPLE 5

A gel containing 10 percent DHA is prepared using the following components:

| Part | Grams | Component |
|---|---|---|
| A | 53.30 | Water |
|   | 1.50 | Polyquaternium-10 |
| B | 20.00 | Alcohol SD40-2 |
| C | 0.18 | Water |
|   | 0.02 | Citric acid |
| D | 15.00 | Water |
|   | 10.00 | Dihydroxyacetone |

The polymer of part A is slowly added, with constant stirring, to the water of that part; mixing is continued until the mixture is thick. Alcohol of part B is slowly mixed into the thick mixture. Citric acid is dissolved in the water of part C and stirred into the mixture. Finally, the DHA is dissolved in the water of part D and combined with the mixture. The polyquaternium 10 can be obtained from Amerchol Corporation as Ucare Polymer JR-30M™.

EXAMPLE 6

A lotion is prepared using the following components:

| Part | Grams | Component |
|---|---|---|
| A | 61.32 | Water |
| B | 10.00 | Emulsifying wax |
| C | 10.00 | n-Dodecylamine |
|   | 10.00 | Propylene glycol |
| D | 7.28 | Water |
|   | 1.40 | Citric acid |

The water of part A is heated to 70° C., and the wax of part B is heated to 70° C. The heated components are combined, with rapid mixing, and cooled to 45° C. with mixing. The dodecylamine is heated to liquefaction and mixed into the propylene glycol, then the mixture is combined with the previous components. The combination is cooled to 35° C. The citric acid of part D is dissolved in the water of that part, and the solution is added to the preceding components, to adjust the pH of the composition to about 9.0 to 9.5.

The emulsifying wax is sold as Polawax™ by Croda Inc., New York, N.Y. U.S.A.

EXAMPLE 7

A lotion is prepared, using the following components:

| Part | Grams | Component |
|---|---|---|
| A | 62.00 | Water |
| B | 15.00 | Emulsifying wax |
|   | 1.00 | n-Hexadecyl alcohol |
|   | 2.00 | Polyoxyethylene(10)oleyl ether |
| C | 10.00 | n-Dodecylamine |
| D | 1.75 | Citric acid |
|   | 5.00 | Water |
| E | 3.25 | Water |

The water of part A is heated to 70° C. The components of part B are combined, heated to 70° C., and the dodecylamine is added. All preceding components are combined, with vigorous mixing, and cooled to 45° C. The citric acid is dissolved in the water of part D and added to the preceding components, to obtain a pH about 9. The water of part E is then combined with the other components.

The emulsifying wax is Polawax™, sold by Croda Inc. The polyoxyethylene(10)oleyl ether is sold by ICI Americas Inc., Wilmington, Del. U.S.A. as Brij 97™.

EXAMPLE 8

A lotion is prepared, using the following components:

| Part | Grams | Component |
|---|---|---|
| A | 60.20 | Water |
|   | 1.18 | Polyoxyethylene(10)cetyl ether |
| B | 6.50 | Polyoxyethylene fatty alcohol ethers |
|   | 0.82 | Polyoxyethylene(2)cetyl ether |
|   | 0.30 | n-Hexadecyl alcohol |
|   | 5.00 | Isopropyl palmitate |
| C | 15.00 | Water |
|   | 10.00 | Dihydroxyacetone |
| D | 1.00 | Biocide |

The part A components are mixed and heated to about 75° C. The part B components are mixed and heated to about 75° C. to form a solution. Parts A and B components are combined with vigorous mixing, then cooled to about 50° C. The DHA is dissolved in the water of part C, and combined with preceding components. Finally, the biocide is mixed into the preparation.

The polyoxyethylene(10)cetyl ether and polyoxyethylene (2)cetyl ether are sold by ICI Americas Inc., Wilmington, Del. U.S.A. as Brij 56™ and Brij 52™, respectively. The polyoxyethylene fatty alcohol ethers are sold by Amerchol Corp., Edison, N.J. U.S.A. as Promulgen G™.

EXAMPLE 9

A lotion is prepared, as in the preceding example, except that 65.2 grams of water are used in part A and the isopropyl palmitate is omitted.

EXAMPLE 10

An alcoholic solution is prepared by mixing 70 milliliters of SD-40 alcohol with 10 grams of n-Dodecylamine, adjusting the pH to 9.0 with concentrated hydrochloric acid, then adjusting the volume to 100 milliliters with additional alcohol.

EXAMPLE 11

An alcoholic solution is prepared by dissolving 10 grams of Dihydroxyacetone in 50 milliliters of water, and diluting to 100 milliliters with SD-40 alcohol.

EXAMPLE 12

The color formed by treating skin (5 cm×5 cm) with 25 microliters of an amine formulation and 25 microliters of a DHA formulation is studied. In each test, the first applied formulation is well rubbed into the skin, then the second is promptly rubbed into the skin. In each test, skin which is originally measured to be outside the tanning target area acquires a color within the target area and with appropriate values of L*, when measured four hours after application of the formulations.

The following combinations of formulations from preceding examples are tested:

| Amine, Example No. | DHA, Example No. |
| --- | --- |
| 1 | 4 |
| 2 | 5 |
| 3 | 5 |
| 6 | 5 |
| 6 | 8 |
| 6 | 9 |
| 7 | 8 |
| 7 | 9 |
| 10 | 11 |

EXAMPLE 13

Tests are conducted to determine the relative substantivity of color formed by the use of DHA and amine formulations of preceding examples. Substantivity is determined by measurement of color before and after a 10×8 centimeter, 500-gram block, fitted with a towel covering its lower surface, is pulled across the skin through five cycles, using a back-and-forth motion. This test is conducted both with the towel dry, and saturated with water.

In all cases, DHA and amine formulations are applied to skin immediately after readings are taken with the Minolta Chroma Meter, using 25 microliters of each formulation on a 25 cm² skin area. A period of seven hours is allowed for color development, then readings are again taken; the difference in total color is termed "Initial $\Delta E$" for the tables which follow. After each of dry and wet rubbing, measurements are made and $\Delta E$ is again determined. Thus, $\Delta E$ always represents total color difference between treated and untreated skin. The following equation is used to calculate $\Delta E$:

$$[(L*_u - L*_T)^2 + (a*_u - a*_T)^2 + (b*_u - b*_T)^2]^{1/2}$$

where the subscripts "U" represent readings with untreated skin and the subscripts "T" represent readings with treated skin.

Results are as shown below, indicating that: (1) about two to three times more total color is formed after seven hours when both amine and DHA are applied, as compared to only DHA applications; and (2) the presence of amine improves resistance to both dry and wet rubbing. All results are averages for four subjects. Visually, differences in $\Delta E$ amounting to at least about 0.5 can be discerned by a trained observer.

| Amine | DHA | $\Delta E$ | | |
| --- | --- | --- | --- | --- |
| No. | No. | Initial | Dry | Wet |
| 7 | 9 | 8.9 ± 1.5 | 8.5 ± 1.6 | 6.4 ± 1.0 |
| 2 | 5 | 10.8 ± 1.5 | 9.8 ± 1.3 | 7.6 ± 1.3 |
| 10 | 11 | 10.4 ± 1.9 | 9.7 ± 1.7 | 6.4 ± 1.2 |
| — | 9 | 5.7 ± 1.3 | 5.0 ± 1.2 | 4.9 ± 1.3 |
| — | 5 | 5.2 ± 1.2 | 4.9 ± 1.4 | 4.6 ± 1.2 |
| — | 11 | 4.1 ± 1.0 | 3.8 ± 0.9 | 3.4 ± 0.7 |

EXAMPLE 14

Substantivity to water rinsing indicates the water solubility of the color formed. A suitable test involves measuring skin color, applying formulations to the skin, allowing color to develop for about six hours, then repeating the color intensity measurement. A gentle stream of luke-warm tap water is allowed to flow over the treated skin for two minutes, then the skin is dried by gently patting with dry paper towels, taking care to not rub the skin. A final skin color measurement is then taken, thirty minutes later. Values of $\Delta E$ can be calculated, as in the preceding example.

The following results are obtained with various amines plus DHA, as compared with DHA only. The amine "MAD" is n-Dodecylamine, formulated as in preceding Example 2. Glycine is used as an aqueous solution containing 4.1 percent of the amino acid, and adjusted to pH 9.0 with hydrochloric acid. The n-Butylamine is a 2.1 percent solution in 50 percent by volume ethanol, 50 percent by volume water, adjusted to pH 9.0. The n-Octylamine is a 3.5 percent solution in a similar 50 volume percent ethanol, adjusted to pH 9.1. Cetyl amine is 6.6 percent n-Hexadecylamine in ethanol, adjusted to pH 9.3. The DHA is formulated according to preceding Example 5, for the glycine and MAD tests (25 microliters of each formulation applied to 25 cm² of skin), and according to preceding Example 4 for the butyl, octyl and cetyl amine tests (10 microliters of each formulation applied to 6.25 cm² of skin).

In the results, "% Color Remaining" is calculated by the equation ($\Delta E_{RINSED}/\Delta E_{UNRINSED} \times 100$) for the application of both amine and DHA formulations, while "Color Increase" is calculated from ($\Delta E_{RINSED}/\Delta E_{DHA-UNRINSED}$), representing the color increase over unrinsed applications of only DHA.

| Amine | Subject | % Color Remaining | Color Increase |
| --- | --- | --- | --- |
| MAD | 1 | 97 | 2.1 |
|  | 2 | 100 | 3.9 |
|  | 3 | 88 | 1.8 |
| Glycine | 1 | 55 | .78 |
|  | 2 | 64 | .88 |
| Butyl | 1 | 49 | .73 |
| Octyl | 1 | 90 | 1.7 |
| Cetyl | 1 | 72 | 1.9 |

EXAMPLE 15

A test similar to that of the preceding example is conducted to compare the substantivity of an aliphatic amine and two α-amino acids. A 1.11 molar DHA formulation as in preceding Example 5 is used, together with one of the following formulations: 0.54 molar lysine in 50 percent by volume aqueous ethanol, adjusted to pH 9.0; 0.54 molar methionine sulfoxide (MSO) in water, adjusted to pH 9.0; or 0.54 molar n-Dodecylamine (MAD) in ethanol, adjusted to pH 9.0. In each case, 25 microliters each of DHA and amine formulations are used on 25 cm² of skin, readings are taken after four hours of color development, water is allowed to flow over the test sites for two minutes, and readings are taken again after patting dry and air drying for thirty minutes.

Results are as follows:

| Amine | % Color Remaining | Color Increase |
|---|---|---|
| Lysine | 25.3 | 0.5 |
| MSO | 36.2 | 1.1 |
| MAD | 87.0 | 4.0 |

EXAMPLE 16

A test is conducted to demonstrate the more rapid color development obtained when skin is treated with both DHA and amine. Two 25 cm$^2$ areas are marked on the skin of two subjects. Both areas are treated with 25 microliters of the DHA formulation of preceding Example 5, and one of the areas is additionally treated with 25 microliters of the amine formulation of preceding Example 2. Values of ΔE are determined at hourly intervals for a period of seven hours. The results are as presented below, wherein the data are derived from the equation ($\Delta E_{AMINE+DHA}/\Delta E_{DHA}$):

| Hours | Subject 1 | Subject 2 |
|---|---|---|
| 0 | 0 | 0 |
| 1 | 3.9 | 5.4 |
| 2 | 7.2 | 13.8 |
| 3 | 3.5 | 4.7 |
| 4 | 3.8 | 3.6 |
| 5 | 3.1 | 3.6 |
| 6 | 3.3 | 2.5 |
| 7 | 2.7 | 2.0 |

Although not shown in these data, the color is noticeably darker at each measurement for the areas also treated with amine.

EXAMPLE 17

The following amines are incorporated into formulations, as with other amines in the preceding examples, and applied to skin with DHA to provide a simulated tan. Each amine has the general formula H$_2$N—(CH$_2$)$_x$-Z, where x and Z are as indicated.

| Amine | x | Z |
|---|---|---|
| 2-(2-Aminoethoxy) ethanol | 2 | O(CH$_2$)$_2$OH |
| 6-Amino-1-hexanol | 6 | OH |
| 2,2-Diethoxyethylamine | 1 | CH(OCH$_2$CH$_3$)$_2$ |
| 3-Aminopropyltriethoxy-silane | 3 | Si(OCH$_2$CH$_3$)$_3$ |
| 3-Aminopropyltrihydroxy-silane | 3 | Si(OH)$_3$ |
| 8-Aminooctanoic acid | 8 | COOH |
| Furfurylamine | 1 | (C$_4$H$_3$O) |
| Tetrahydrofurfurylamine | 1 | (C$_4$H$_7$O) |
| Benzylamine | 1 | (C$_6$H$_5$) |
| 2-Aminoacetophenone | 1 | C(O) (C$_6$H$_5$) |
| Triethyleneglycol diamine | 2 | (OCH$_2$CH$_2$)$_2$NH$_2$ |
| Tetraethyleneglycol diamine | 2 | (OCH$_2$CH$_2$)$_3$NH$_2$ |

The invention has been described with respect to several specific embodiments, but is not to be limited to those embodiments, the scope of the invention being defined only by the appended claims. Various improvements, alternatives and equivalents will be apparent to those skilled in the art upon reading the foregoing description and examples, and such are included within the claimed invention.

What is claimed is:

1. Apparatus for imparting artificial tan to skin, comprising:
   (a) a receptacle containing a fluid formulation comprising dihydroxyacetone;
   (b) a receptacle containing a fluid formulation comprising a primary amine, provided that the amine is not an α-amino acid; and
   (c) dispensing means for simultaneously or sequentially providing desired amounts of dihydroxyacetone and amine.

2. The apparatus of claim 1, wherein at least one of dihydroxyacetone and amine is present in a solution.

3. The apparatus of claim 1, wherein at least one of dihydroxyacetone and amine is present in an emulsion.

4. The apparatus of claim 1, wherein at least one of dihydroxyacetone and amine is present in a gel.

5. The apparatus of claim 1, wherein the dispensing means provides molar ratios of dihydroxyacetone to amine about 0.5 to about 10.

6. The apparatus of claim 5, wherein there are provided molar ratios of dihydroxyacetone to amine about 1 to about 5.

7. The apparatus of claim 5, wherein there are provided molar ratios of dihydroxyacetone to amine about 1 to about 3.

8. The apparatus of claim 1 wherein at least one formulation establishes pH values about 3 to about 13, when desired amounts of the formulations are mixed.

9. The apparatus of claim 8, wherein pH values about 7 to about 11 are established.

10. The apparatus of claim 8, wherein pH values about 9 to about 10 are established.

11. The apparatus of claim 1, wherein the amine has the formula RNH$_2$, in which R is selected from the group consisting of:
—(CH$_2$)$_n$COOH;
—(CH$_2$)$_x$COOR';
—(CH$_2$)$_y$CH$_3$;
—(CH$_2$)$_x$OH;
—CH$_2$(C$_6$H$_5$);
—C(O)(C$_6$H$_5$);
—(CH$_2$)$_x$CH(OR')$_2$;
—(CH$_2$)$_x$OR';
—(OCH$_2$CH$_2$)$_z$NH$_2$;
cyclic groups containing N, O or S in the ring;
—Si(OH)$_3$; and
—Si(OR')$_3$;
wherein n is an integer of at least 2, x is an integer of up to 22, y is an integer of 5 to about 22, z is an integer of up to about 10, and R' is an alkyl group having up to about 10 carbon atoms.

12. A method for imparting artificial tan to human skin, comprising contacting the skin with dihydroxyacetone and a primary amine having the formula RNH$_2$, wherein R is selected from the group consisting of:
—(CH$_2$)$_n$COOH;
—(CH$_2$)$_x$COOR';
—(CH$_2$)$_y$CH$_3$;
—(CH$_2$)$_x$OH;
—CH$_2$ (C$_6$H$_5$);
—C(O)(C$_6$H$_5$);
—(CH$_2$)$_x$CH(OR')$_2$;
—(CH$_2$)$_x$OR';

—$(OCH_2CH_2)_zNH_2$;

cyclic groups containing N, O or S in the ring;

—$Si(OH)_3$; and

—$Si(OR')_3$;

wherein n is an integer of at least 2, x is an integer of up to 22, y is an integer of 5 to about 22, z is an integer of up to about 10, and R' is an alkyl group having up to about 10 carbon atoms.

13. The method of claim 12, wherein the dihydroxyacetone and amine are applied to skin sequentially.

14. The method of claim 12, wherein the dihydroxyacetone and amine are applied to skin substantially simultaneously.

15. The method of claim 12, wherein a formulation containing dihydroxyacetone and amine is applied to skin.

16. The method of claim 12, wherein pH values between about 3 and about 13 are established as skin is initially contacted.

17. The method of claim 16, wherein pH values between about 7 and about 11 are established.

18. The method of claim 16, wherein pH values between about 9 and about 10 are established.

19. The method of claim 12, wherein the molar ratio of dihydroxyacetone to amine is about 0.5 to about 10.

20. The method of claim 12, wherein the molar ratio of dihydroxyacetone to amine is about 1 to about 5.

21. The method of claim 12, wherein the molar ratio of dihydroxyacetone to amine is about 1 to about 3.

22. A composition for immediate application to skin, comprising a mixture of:

(a) a formulation containing dihydroxyacetone; and (b) a formulation containing a primary amine having the formula $RNH_2$, wherein R is selected from the group consisting of:

—$(CH_2)_nCOOH$;

—$(CH_2)_xCOOR'$;

—$(CH_2)_yCH_3$;

—$(CH_2)_xOH$;

—$CH_2(C_6H_5)$;

—$C(O)(C_6H_5)$;

—$(CH_2)_xCH(OR')_2$;

—$(CH_2)_xOR'$;

—$(OCH_2CH_2)_zNH_2$;

cyclic groups containing N, O or S in the ring;

—$Si(OH)_3$; and

—$Si(OR')_3$;

wherein n is an integer of at least 2, x is an integer of up to 22, y is an integer of 5 to about 22, z is an integer of up to about 10, and R' is an alkyl group having up to about 10 carbon atoms.

* * * * *